(12) United States Patent
Tsuji et al.

(10) Patent No.: US 9,445,727 B2
(45) Date of Patent: Sep. 20, 2016

(54) APPARATUS FOR EVALUATING VASCULAR ENDOTHELIAL FUNCTION

(71) Applicants: HIROSHIMA UNIVERSITY, Tokyo (JP); NIHON KOHDEN CORPORATION, Tokyo (JP)

(72) Inventors: Toshio Tsuji, Higashi-Hiroshima (JP); Masao Yoshizumi, Hiroshima (JP); Yukihito Higashi, Hiroshima (JP); Masashi Kawamoto, Hiroshima (JP); Hideo Ozawa, Tokyo (JP); Teiji Ukawa, Tokyo (JP); Tsuneo Takayanagi, Tokyo (JP); Haruka Morimoto, Tokyo (JP); Ryosuke Kubo, Higashi-Hiroshima (JP)

(73) Assignees: HIROSHIMA UNIVERSITY, Tokyo (JP); NIHON KOHDEN CORPORATION, Tokyo (JP)

( * ) Notice: Subject to any disclaimer, the term of this patent is extended or adjusted under 35 U.S.C. 154(b) by 705 days.

(21) Appl. No.: 13/712,104

(22) Filed: Dec. 12, 2012

(65) Prior Publication Data
US 2013/0158419 A1 Jun. 20, 2013

(30) Foreign Application Priority Data
Dec. 19, 2011 (JP) .................... 2011-276925

(51) Int. Cl.
*A61B 5/02* (2006.01)
*A61B 5/021* (2006.01)
(Continued)

(52) U.S. Cl.
CPC ......... *A61B 5/02007* (2013.01); *A61B 5/0225* (2013.01); *A61B 5/02108* (2013.01); *A61B 5/02233* (2013.01); *A61B 5/7242* (2013.01); *A61B 5/7278* (2013.01)

(58) Field of Classification Search
CPC combination set(s) only.
See application file for complete search history.

(56) References Cited

U.S. PATENT DOCUMENTS 6,719,704 B2 4/2004 Narimatsu et al.
6,939,304 B2 9/2005 Schnall et al.
(Continued)

FOREIGN PATENT DOCUMENTS

CN 101495033 A 7/2009
EP 2294976 A1 3/2011
(Continued)

OTHER PUBLICATIONS

Search Report dated Apr. 3, 2013 issued by the European Patent Office in counterpart European Application No. 12196716.0.
(Continued)

*Primary Examiner* — Michael Kahelin
*Assistant Examiner* — Mitchell E Alter
(74) *Attorney, Agent, or Firm* — Sughrue Mion, PLLC

(57) ABSTRACT

An apparatus for evaluating a vascular endothelial function, includes: a cuff pressure controlling unit configured to perform continuous pressure stimulation on a part of a body of a subject for a predetermined time, by using a cuff adapted to be wrapped around the part of the body of the subject; a cuff pressure detecting unit configured to detect a cuff pressure from an output of a pressure sensor connected to the cuff; a pulse wave detecting unit configured to detect a pulse wave from the output of the pressure sensor; and an analyzing unit configured to evaluate the vascular endothelial function by comparing vessel viscoelastic indexes which are obtained from the pulse wave detected in two of zones before, during, and after the pressure stimulation, and which exclude an amplitude of the pulse wave.

16 Claims, 10 Drawing Sheets

(51) Int. Cl.
*A61B 5/00* (2006.01)
*A61B 5/022* (2006.01)
*A61B 5/0225* (2006.01)

(56) References Cited

U.S. PATENT DOCUMENTS

| | | | | |
|---|---|---|---|---|
| 2001/0016690 | A1* | 8/2001 | Chio | A61B 5/02007 600/485 |
| 2003/0216652 | A1* | 11/2003 | Narimatsu et al. | 600/490 |
| 2005/0070805 | A1* | 3/2005 | Dafni | 600/492 |
| 2005/0107710 | A1 | 5/2005 | Nakayama | |
| 2005/0228303 | A1* | 10/2005 | Hayano et al. | 600/504 |
| 2009/0259131 | A1* | 10/2009 | Tsuji et al. | 600/493 |
| 2009/0306523 | A1 | 12/2009 | Saito et al. | |
| 2011/0066048 | A1* | 3/2011 | Tsuji et al. | 600/490 |

FOREIGN PATENT DOCUMENTS

| | | |
|---|---|---|
| JP | 3632014 B2 | 12/2004 |
| JP | 2006-181261 A | 7/2006 |
| JP | 2006-263354 A | 10/2006 |
| JP | 2007-209492 A | 8/2007 |
| JP | 4049671 B2 | 12/2007 |
| JP | 2008-29690 A | 2/2008 |
| JP | 2008-161644 A | 7/2008 |
| JP | 2009-273870 A | 11/2009 |
| JP | 2011-056200 A | 3/2011 |
| JP | 2011-182968 A | 9/2011 |
| JP | 2011-189080 A | 9/2011 |
| WO | 2010/134233 A1 | 11/2010 |

OTHER PUBLICATIONS

Communication dated Jun. 30, 2015 issued by the Japanese Patent Office in counterpart Japanese Patent Application No. 2011-276925.
Communication dated Sep. 28, 2015 issued by the State Intellectual Property Office of the People's Republic of China in counterpart Chinese Patent Application No. 201210537440.1.
Communication dated Jan. 19, 2016, from the Japanese Patent Office in counterpart application No. 2011-276925.
Communication issued Jun. 3, 2016, issued by the State Intellectual Property Office of the People's Republic of China in counterpart Chinese Patent Application No. 201210537440.1.

* cited by examiner

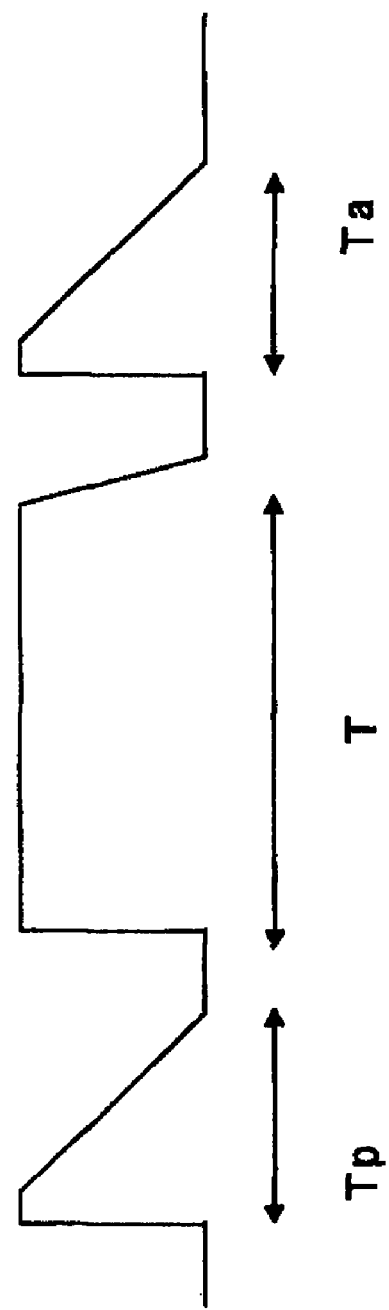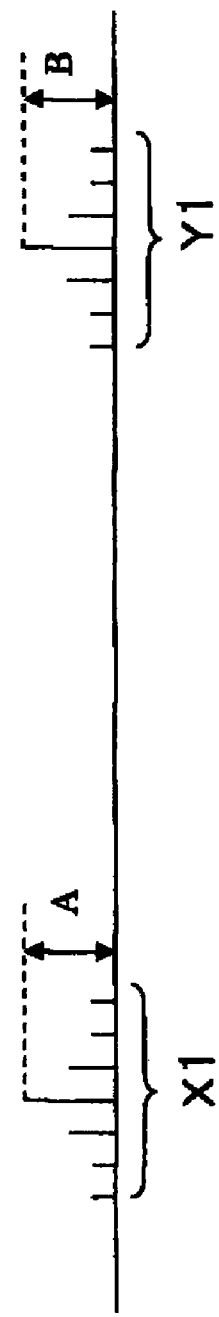
FIG. 3A
FIG. 3B

APPARATUS FOR EVALUATING VASCULAR ENDOTHELIAL FUNCTION

CROSS-REFERENCE TO RELATED APPLICATION(S)

This application is based upon and claims the benefit of priority from prior Japanese patent application No. 2011-276925, filed on Dec. 19, 2011, the entire contents of which are incorporated herein by reference.

BACKGROUND

The presently disclosed subject matter relates to an apparatus for evaluating a vascular endothelial function in which the evaluation similar to that obtained in a measurement using an ultrasonic echo system is enabled without using an ultrasonic echo system or the like.

Recently, researches that arteriosclerosis develops while showing deterioration of the vascular endothelial function as the initial phase have been conducted. In order to prevent arteriosclerosis, techniques and apparatuses for evaluating the vascular endothelial function have been developed.

As a reliable technique for evaluating the vascular endothelial function, there is an apparatus called an FMD (Flow-Mediated Dilation) measurement system. In the apparatus, measurement is performed in the following manner. A cuff which is similar to that for measuring the blood pressure is attached to the arm of the subject. After occlusion of the artery is performed for a constant time of about five minutes at a pressure which is higher than the maximal blood pressure of the subject, the occlusion of the artery is released. At about three minutes after the release of the occlusion of the artery, the vessel diameter at the upstream or downstream of the cuff is measured by an ultrasonic echo system. Based on the time-dependent change rate of the vessel diameter, the vascular endothelial function is evaluated.

In the case of a normal vessel, the production of NO which is a vasodepressor material from vascular endothelial cells is promoted by shear stress of the inner wall of the vessel due to a blood flow immediately after the occlusion of the artery. As a result, the vessel diameter is expanded. By contrast, in the case where a disorder exists in the vascular endothelial function, the degree of the expansion of the vessel diameter is decreased. When the change in vessel diameter before and after the occlusion of the artery is measured, therefore, it is possible to evaluate the vascular endothelial function.

The evaluation technique by the FMD measurement system requires skills in measurement of the vessel diameter by an ultrasonic echo system, and is difficult to handle. Furthermore, there is a problem in that the technique requires a large-scale apparatus and lacks in simplicity.

By contrast, as a technique using a simple configuration, there is a technique using a cuff pressure. In the technique, the cuff pressure is maintained at a predetermined pressure which is higher than the maximal blood pressure, thereafter rapidly lowered, maintained at another predetermined pressure which is higher than the minimal blood pressure and lower than the mean blood pressure, and, during when the cuff pressure is maintained at the other predetermined pressure, a ratio of a cuff pressure peak value of a first pulse wave which initially appears to the maximal cuff pressure peak value which thereafter appears is calculated, thereby enabling the vascular endothelial function to be evaluated (see JP-A-2007-209492).

As a technique in which an index of the vascular endothelial function can be accurately measured by a simple method, there is a technique in which pressure and volume pulse waves of a vessel to be measured are measured, a ratio of variations of the pulse waves per unit time is obtained, and, with respect to the third root of the maximum value of the ratio of variations of one heartbeat cycle at rest, a ratio to a value after release of occlusion of the artery is calculated as the degree of vasodilation (see JP-A-2006-181261).

There is another technique in which, based on the time-dependent change of posterior pulse wave information indicating a feature of the posterior half portion which is after the peak of a pulse wave reflecting variations of the vessel diameter, it is determined whether the function of vascular endothelial cells is normal or not (see Japanese Patent No. 3,632,014).

There is a further technique in which a digit probe for measuring a change of the peripheral arterial pulsatile flow is attached to a finger tip, occlusion of the artery is performed for a constant time period while attaching a cuff to the same finger tip, and a change of the peripheral arterial tone before and after the occlusion of the artery is monitored by the digit probe (see Japanese Patent No. 4,049,671).

In the FMD method, the measurement is performed by using the ultrasonic echo system, and skills are required to measure the vessel diameter. In the presently disclosed subject matter, by contrast, a change in vascular volume before and after the pressure stimulation is measured, so that information which is equivalent to that obtained in the FMD method that is a reliable related art technique can be easily obtained, and the measurement can be performed by a technique and configuration which are similar to those of the blood pressure measurement that is currently widely performed, so that skills are not required.

In the technique disclosed in JP-A-2007-209492, the pressurization periods for the pressure stimulation and the pulse wave measurement are continuous to each other. Although the pressurization for the pulse wave measurement is lower than the artery mean blood pressure, the vein blood flow is blocked, and hence the burden on the subject is large. In the presently disclosed subject matter, by contrast, an idle period when the cuff pressurization is stopped exists between the pressure stimulation and the pulse wave measurement. Therefore, a continuous vessel blocking period is kept to the minimum, so that the burden on the subject can be reduced.

In the technique disclosed in JP-A-2006-181261, in addition to the cuff for the pressure stimulation, a sensor for measuring the volume and pressure pulse waves must be disposed. Therefore, the operation is complicated. In the presently disclosed subject matter, by contrast, a sensor other than the attachment of the cuff is not necessary. Consequently, the presently disclosed subject matter is advantageous in operation.

In the technique disclosed in Japanese Patent No. 3,632,014, a reflected wave component which is contained in the pressure pulse wave, and which is originated from peripheral vessels is measured. Measurement of the reflected wave component and calculation of an amplitude augmentation factor AI necessitate complicated waveform recognizing and calculating processes, and an analyzing unit must have a high processing capacity. In the presently disclosed subject matter, by contrast, it is requested only to measure the waveform of a pulse wave, and hence an analyzing unit is not required to have a high processing capacity.

The vascular compliance is changed by the blood pressure. When the blood pressure is high, the vessel wall is in a state where the wall is extended in the circumferential direction and hardened, and the compliance is low. Conversely, when the blood pressure is low, a force acting on the vessel wall is small. Therefore, the vessel wall is extended in a smaller degree in the circumferential direction, and the compliance is high. All of the techniques disclosed in JP-A-2007-209492, JP-A-2006-181261 and Japanese Patent No. 3,632,014 have a problem in that the measured vessel information is inevitably affected by the intravascular pressure, i.e., the blood pressure.

In the technique disclosed in Japanese Patent No. 4,049, 671, a change of the peripheral arterial tone is monitored by the digit probe. In the case where amplitudes of pulse waves are compared to each other, however, the possibility that unwanted influences are included is high. Particularly, the peripheral arterial tone is caused also by the sympathetic control. Consequently, there is a problem in that the technique cannot always correctly detect the vascular endothelial function.

In the related art, the cuff pressure indicating the maximum pulse wave amplitude corresponds to the mean blood pressure. Irrespective of the level of the blood pressure, when a vessel is compressed by a cuff at a pressure which is equal to the mean blood pressure, the pressures internal and external of the vessel counteract each other, and the force acting in the circumferential direction of the vessel wall is minimized. The maximum pulse wave amplitude which is measured in the presently disclosed subject matter is always measured in a state where the force acting in the circumferential direction of the vessel wall is minimum, and therefore the influence of the level of the blood pressure on the measurement result is reduced. It can be said that a change in vessel diameter in this state indicates the characteristics of the vessel wall itself.

In view of the above-discussed circumstances, the inventors have proposed an apparatus and the like in which a cuff is wrapped around a part of the body such as an arm, occlusion of the artery is performed for a predetermined time period by using the cuff, the pulse wave is detected by using the cuff at the same position before and after the occlusion of the artery or the like, and the detected pulse wave is analyzed to evaluate the vascular endothelial function (see JP-A-2009-273870 and JP-A-2011-56200).

It has been proved that, according to the apparatus, the vascular endothelial function can be adequately evaluated by using a cuff. Thereafter, the inventors have intensively studied, and obtained the conclusion that, in the techniques disclosed in JP-A-2009-273870 and JP-A-2011-56200, the influence due to the blood pressure can be reduced by measuring the maximum pulse wave amplitude in the case where the cuff pressure is changed, but this measurement is probably performed merely on one of the viscoelastic characteristics of the vessel. When a change occurs in the vessel wall viscosity, therefore, a change appears in the response characteristics of the vessel wall, in addition to a change in the pulse wave amplitude. In the techniques disclosed in JP-A-2009-273870 and JP-A-2011-56200, however, there is a possibility that such a change cannot be sufficiently captured. It has been considered that a comparison of viscoelastic indexes of the vessel (hereinafter, such an index is referred to as "vessel viscoelastic index") other than the maximum pulse wave amplitude is effective in solving the problem.

In a case where the structure of the artery wall is expressed by the Voigt model, the following expression holds for the stress f and the distortion x:

$$f = ex + r(dx/dt) \qquad (1)$$

where e is the elastic constant and r is the viscosity constant.

It is considered that the distortion x in Expression (1) corresponds to the change in the vessel diameter in the techniques disclosed in JP-A-2009-273870 and JP-A-2011-56200, and the techniques disclosed in JP-A-2009-273870 and JP-A-2011-56200 in which the ratio of maximum pulse wave amplitudes are obtained are those mainly related to indexes of the portion of Expression (1) indicating all of the vessel viscoelastic indexes, excluding the derivative term of the right side. Therefore, it is requested to develop an apparatus for evaluating a vascular endothelial function which uses the indexes related to Expression (1) indicating all of the vessel viscoelastic indexes, excluding the maximum pulse wave amplitude.

The related-art FMD measures the DC component (the distortion x in Expression (1)) of the vessel diameter in synchronization with the QRS of an electrocardiogram, in principle does not measure the pulsation component, and therefore is not affected by the viscosity of the vessel wall. As apparent from Expression (1), however, the evaluation technique in the presently disclosed subject matter which uses the vessel viscoelastic indexes, and which is related to the vascular endothelial function is affected by the viscosity (r(dx/dt) in Expression (1)) of the vessel wall. When an apparatus for evaluating a vascular endothelial function in which an evaluation similar to that obtained in a measurement using an ultrasonic echo system is enabled is to be developed, therefore, the influence of the viscosity must be reduced as far as possible.

FIG. 9 shows results of measurements of changes of the elasticity and the viscosity in the vasolidation before and after the pressure stimulation, by the related-art FMD. According to FIG. 9, it is seen that the elasticity after the pressure stimulation is decreased as compared to that before the pressure stimulation, and the viscosity after the pressure stimulation is increased as compared to that before the pressure stimulation.

FIG. 10 shows examples of the amplitude waveform of the pulse wave in measurements in cases where only the elasticity was decreased, and where the elasticity was decreased and at the same time the viscosity was increased. According to FIG. 10, when only the elasticity is decreased, only the amplitude of the pulse wave is increased, and it is estimated that, when the amplitude of the pulse wave is measured, the vascular endothelial function can be captured. As shown in the lower portion of FIG. 10, it is seen that, when the elasticity is decreased and the viscosity is simultaneously increased, a time lag occurs in the amplitude change. As a result, it is suggested that, when the elasticity is decreased and the viscosity is simultaneously increased, sufficient determination cannot be performed by means of a measurement of the amplitude change.

SUMMARY

The presently disclosed subject matter may provide an apparatus for evaluating a vascular endothelial function which, even when a change occurs in the vessel viscosity, can accurately evaluate the vascular endothelial function.

The apparatus may comprise: a cuff pressure controlling unit configured to perform continuous pressure stimulation on a part of a body of a subject for a predetermined time, by using a cuff adapted to be wrapped around the part of the body of the subject; a cuff pressure detecting unit configured to detect a cuff pressure from an output of a pressure sensor connected to the cuff; a pulse wave detecting unit configured to detect a pulse wave from the output of the pressure sensor; and an analyzing unit configured to evaluate the vascular endothelial function by comparing vessel viscoelastic indexes which are obtained from the pulse wave detected in two of zones before, during, and after the pressure stimulation, and which exclude an amplitude of the pulse wave.

The vessel viscoelastic indexes which exclude the amplitude of the pulse wave may be one of velocities, areas, accelerations, waveform heights, and peak time periods of the pulse wave detected in the two of zones.

The pressure stimulation may be pressurization at a substantially constant pressure for the predetermined time.

The cuff pressure controlling unit may perform at least one time processing in which, at least one of before and after the pressure stimulation, the cuff pressure is raised from an atmosphere pressure to a pressure that is equal to or higher than a mean blood pressure of the subject, and then lowered to a pressure that is equal to or lower than a minimal blood pressure of the subject.

The analyzing unit may evaluate the vascular endothelial function by comparing a vessel viscoelastic index excluding an amplitude of the pulse wave which is obtained in a constant-pressure process in which a predetermined pressure of the cuff pressure, which is attained in a pressurization process, is maintained for a predetermined time period, with a vessel viscoelastic index excluding an amplitude of the pulse wave which is obtained before or after the pressure stimulation.

The analyzing unit may perform statistical processing on a change of the pulse wave obtained during a change of the cuff pressure.

The statistical processing may be processing in which a maximum value of a vessel viscoelastic index excluding an amplitude of the pulse wave in a process of pressurizing or depressurizing the cuff pressure is obtained.

The statistical processing may be processing in which a maximum value of a vessel viscoelastic index excluding an amplitude of the pulse wave in a constant-pressure process of the cuff pressure is obtained.

The statistical processing may be processing in which an average value of a neighborhood of a maximum value of a vessel viscoelastic index excluding an amplitude of the pulse wave obtained during the change of the cuff pressure is obtained.

The statistical processing may be processing in which an average value of a neighborhood of a maximum value of a vessel viscoelastic index excluding an amplitude of the pulse wave obtained when the cuff pressure is constant is obtained.

The apparatus may further comprise a displaying unit, the analyzing unit may calculate a blood pressure value from the pulse wave, and the displaying unit may display the blood pressure value together with a result of a comparison by the analyzing unit.

The cuff may include a first cuff which is adapted to be wrapped around a first part of the body of the subject, and a second cuff which is adapted to be wrapped around a second part of the body of the subject, the cuff pressure controlling unit may control pressurization and depressurization of one of the first and second cuffs, and the cuff pressure detecting unit may detect the cuff pressure from an output of a pressure sensor connected to the other of the first and second cuffs.

The first and second cuffs may be placed on one of four limbs of the body of the subject.

BRIEF DESCRIPTION OF THE DRAWINGS

FIGS. 3A and 3B are views illustrating first examples of a pulse wave measurement which is performed by the embodiment of the apparatus for evaluating a vascular endothelial function according to the presently disclosed subject matter, and a period of occlusion of the artery.

DETAILED DESCRIPTION OF EXEMPLARY EMBODIMENTS

The inventors of the present application have found that the production of NO which is a vasodepressor material from vascular endothelial cells is promoted by shear stress of the inner wall of the vessel due to a blood flow immediately after occlusion of the artery, with the result that the vessel diameter is expanded and the vessel viscosity is increased.

The relationship between a change in the blood pressure and the vascular volume pulse wave can be expressed by the following expression. According to Boyle's Law, $$P \times V = k \text{ (constant)}$$

where P is the intracuff pressure of a cuff and V is the intracuff volume.

When the vascular volume is increased by ΔV and the intracuff pressure is raised by ΔP, $$(P+\Delta P)\times(V+\Delta V)=k.$$

Here, ΔP×ΔV is sufficiently small, and therefore the following holds:

$$\Delta V=\Delta P\times(V/P).$$

It is seen that, in the case where P and V are constant, the pressure pulse wave ΔP is proportional to the vascular volume change ΔV. Therefore, this show that a change in the vessel diameter can be measured by using the pressure pulse wave, the vessel viscoelastic index of Expression (1) can be obtained, and the evaluation is enabled.

Figure 1:
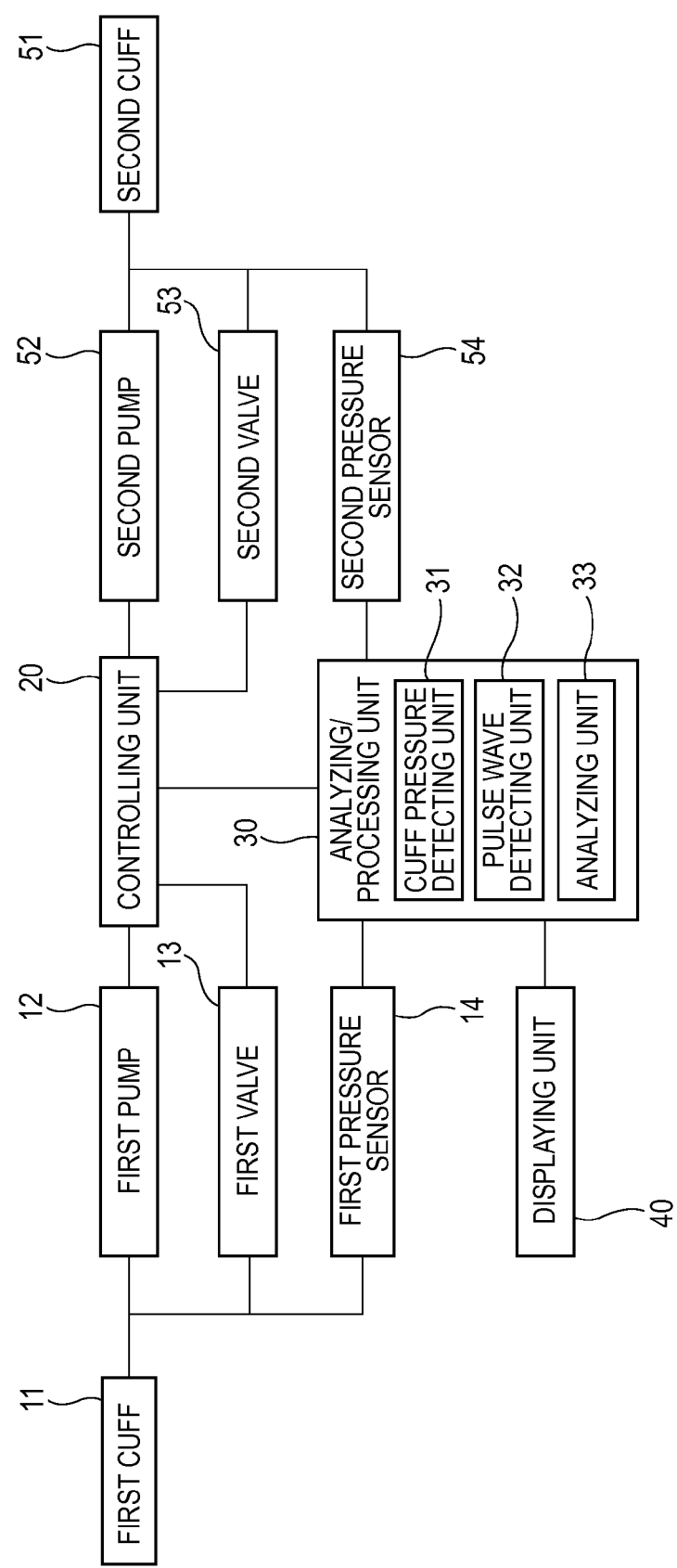
FIG. 1 is a diagram illustrating the configuration of an embodiment of the apparatus for evaluating a vascular endothelial function according to the presently disclosed subject matter.
Figure 2:
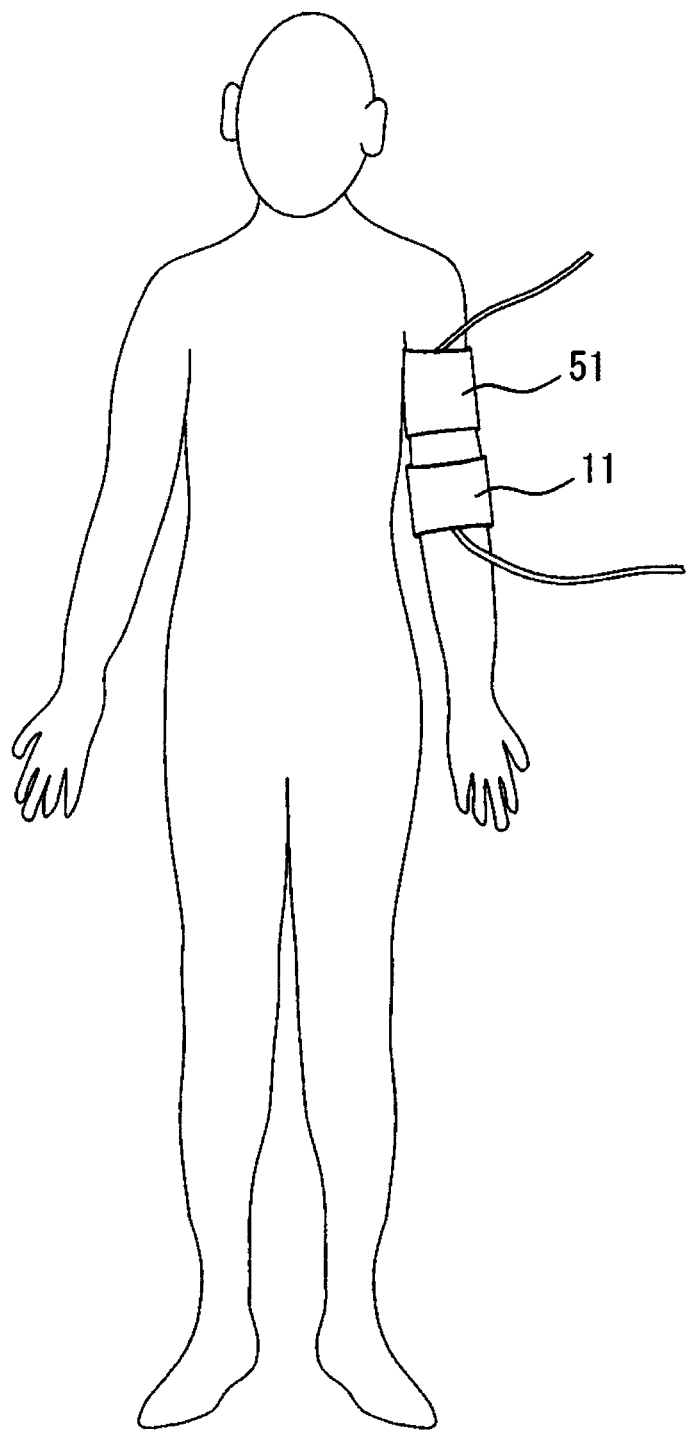
FIG. 2 is a view illustrating a state where cuffs of the apparatus for evaluating a vascular endothelial function according to the presently disclosed subject matter are attached to the body.

Hereinafter, an embodiment of the apparatus for evaluating a vascular endothelial function of the presently disclosed subject matter will be described with reference to the accompanying drawings. In the figures, the identical components are denoted by the same reference numerals, and duplicated description will be omitted. FIG. 1 is a diagram showing the configuration of an apparatus for evaluating a vascular endothelial function according to the embodiment of the presently disclosed subject matter. The apparatus includes a first cuff 11, a first pump 12, a first valve 13, a first pressure sensor 14, a controlling unit 20, an analyzing/processing unit 30, and a displaying unit 40. A second pump 52 and a second valve 53 are connected to the controlling unit 20. A second pressure sensor 54 is connected to the analyzing/processing unit 30. Furthermore, a second cuff 51 is connected to the second pump 52, the second valve 53, and the second pressure sensor 54. The first cuff 11 is to be wrapped around a first body part such as an arm or leg of the subject, and used for applying a pressure for occlusion of the artery on the portion around which the cuff is wrapped. The second cuff 51 is to be wrapped around a second body part such as an arm or leg of the subject, and used for applying a pressure for pulse wave detection on the portion around which the cuff is wrapped. In a measurement, preferably, for example, the first cuff 11 is wrapped around an arm portion of the arm, and the second cuff 51 is wrapped around a portion which is on the upstream side (the side which is closer to the heart) of the first cuff 11 as shown in FIG. 2. The first cuff 11 and the second cuff 51 may be placed on the identical and same-side one of the four limbs of the body of the subject.

The first pump 12 feeds the air into the first cuff 11 under the control of the controlling unit 20. The first valve 13 switches non-discharging/discharging of the air in the first cuff 11 under the control of the controlling unit 20. The second pump 52 feeds the air into the second cuff 51 under the control of the controlling unit 20. The second valve 53 switches non-discharging/discharging of the air in the second cuff 51 under the control of the controlling unit 20. The controlling unit 20 constitutes a cuff pressure controlling unit which controls pressurization and depressurization of the first cuff 11 and the second cuff 51.

The first pressure sensor 14 is connected to the first cuff 11, and outputs a signal corresponding to the pressure in the first cuff 11, and the second pressure sensor 54 is connected to the second cuff 51, and outputs a signal corresponding to the pressure in the second cuff 51. The analyzing/processing unit 30 is configured by, for example, a computer, controls the whole apparatus, and includes a cuff pressure detecting unit 31, a pulse wave detecting unit 32, and an analyzing unit 33. In the embodiment, for the sake of convenience, the controlling unit 20 which controls the first cuff 11 and the second cuff 51, and the analyzing/processing unit 30 which performs analysis and processing are commonly used. Alternatively, they are disposed for each of the cuffs.

The cuff pressure detecting unit 31 detects the cuff pressures of the first and second cuffs 11, 51 from outputs of the first and second pressure sensors 14, 54. The pulse wave detecting unit 32 detects a pulse wave from the output of the second pressure sensor 54. The analyzing unit 33 analyzes the detected pulse wave to perform a comparison using the vessel viscoelastic index which is obtained from pulse waves detected in any two of zones, i.e., before the pressure stimulation, during the pressure stimulation, and after the pressure stimulation, and which excludes the amplitudes of the pulse waves, thereby evaluating the vascular endothelial function.

The controlling unit 20 performs continuous pressure stimulation for a predetermined time period, on a part of the body of the subject, and changes the cuff pressure as shown in, for example, FIG. 3A. Namely, vascular endothelial stimulation is executed during a pressurization period (a period of occlusion of the artery) T by using the first cuff 11, and the pulse wave amplitude is measured before and after the pressurization period T, i.e., during measurement periods Tp and Ta by using the second cuff 51. For example, the pressurization period T may be set to about five minutes, and the measurement periods Tp and Ta may be set to a time which is required for usual blood pressure measurement. During the pressurization period T, the output of the first pressure sensor 14 is monitored, and occlusion of the artery is performed at a pressure which is a sum of the maximal blood pressure and a predetermined pressure (for example, 50 mmHg).

Figure 4:
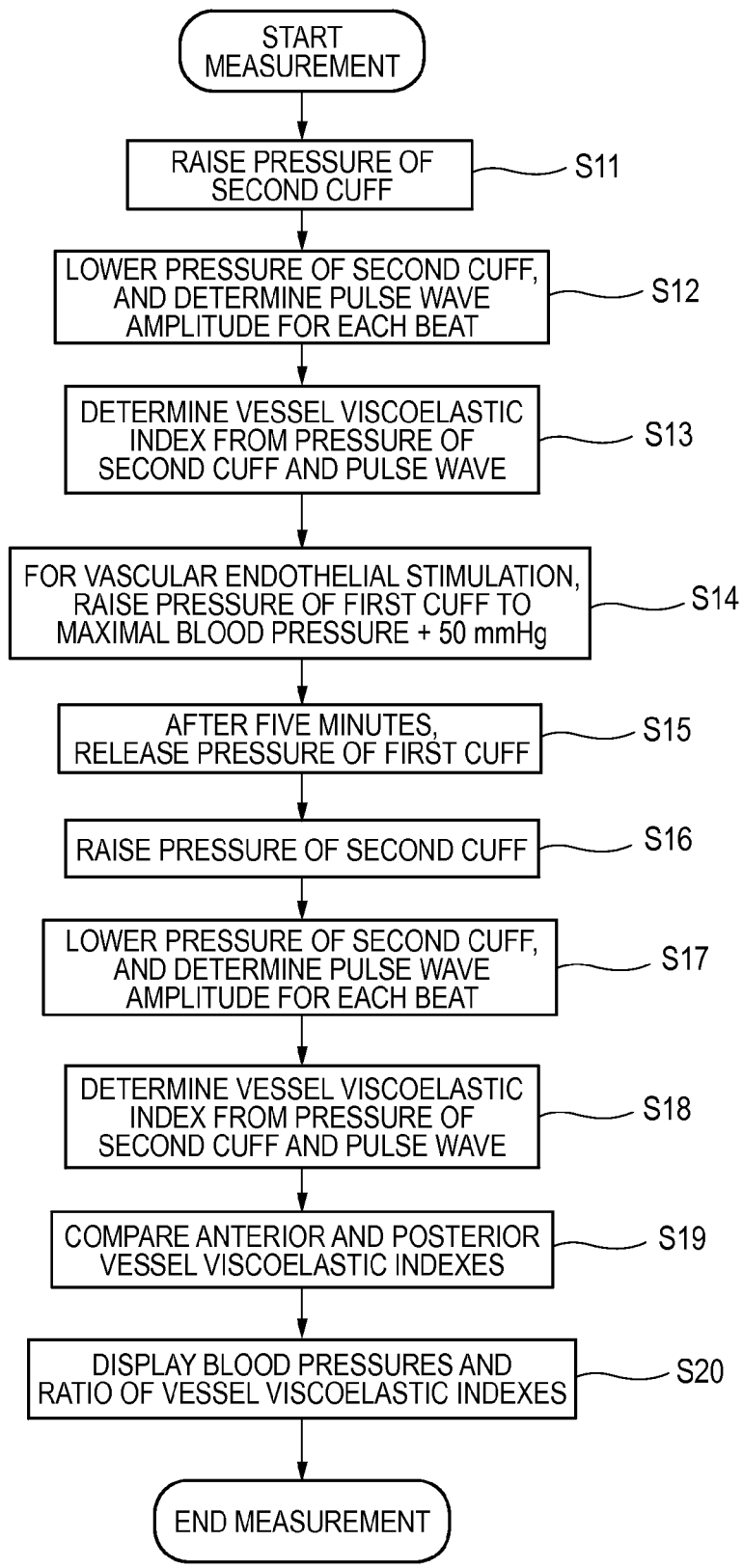
FIG. 4 is a flowchart illustrating a pulse wave measuring operation which is performed in a process of depressurizing a cuff pressure by the embodiment of the apparatus for evaluating a vascular endothelial function according to the presently disclosed subject matter.

The apparatus for evaluating a vascular endothelial function performs processing shown in the flowchart of FIG. 4. As described above, the first cuff 11 is wrapped around an arm portion which is a part of the body of the subject as shown in, for example, FIG. 2, the second cuff 51 is wrapped around an arm portion which is a part of the body of the subject, and which is on the upstream side of the first cuff 11, and then the measurement is started. Under the control of the controlling unit 20, in a state where the second valve 53 is closed, the air is sent from the second pump 52 to the second cuff 51 to raise the cuff pressure (S11).

When the cuff pressure reaches a predetermined pressure, the air supply from the second pump 52 is stopped, and the second valve 53 is opened. Therefore, the cuff pressure is lowered, and the pulse wave detecting unit 32 detects the pulse wave amplitude for each beat (S12).

Furthermore, the cuff pressure detecting unit 31 detects the cuff pressure from the output of the second pressure sensor 54, and, on the basis of the cuff pressure and the pulse wave, the analyzing unit 33 obtains the vessel viscoelastic index (S13). The vessel viscoelastic index is obtained by statistically processing the pulse wave which is obtained in the measurement period Tp. The pulse wave in the measurement period Tp is obtained as shown in FIG. 3B, and hence the area of the pulse wave is obtained as the vessel viscoelastic index. In the measurement period Tp, when the cuff pressure is equal to the mean blood pressure, the pulse wave amplitude is maximum, and hence the maximum area (integral value) is obtained in several waveforms of the pulse wave shown in, for example, FIG. 6B which is an enlarged view of a pulse wave in the vicinity of the maximum pulse wave amplitude shown in FIG. 6A. In the case where the mean blood pressure is previously known, pressurization to a pressure which is equal to or higher than the mean blood pressure is not necessary in order to obtain the maximum pulse wave, and the burden on the subject is reduced.

Next, the pressurization period T when, in a state where the first valve 13 is closed under the control of the controlling unit 20, air is sent from the first pump 12 to the first cuff 11, and, for vascular endothelial stimulation, occlusion of the artery is performed at a pressure which is a sum of the maximal blood pressure and the predetermined pressure (for example, 50 mmHg) is realized (S14). After five minutes, the first valve 13 is opened to release the cuff pressure, whereby the cuff pressure is lowered to a pressure which is equal to or lower than the minimal blood pressure (S15). Thereafter, the second valve 53 is closed, and air is sent from the second pump 52 to raise the cuff pressure (S16). Furthermore, the cuff pressure of the second cuff 51 is lowered in a similar manner as described above, and the pulse wave detecting unit 32 detects the pulse wave amplitude for each beat (S17).

In a similar manner as step S13, on the basis of the cuff pressure and the pulse wave amplitude, the analyzing unit 33 obtains the area of the pulse wave as the vessel viscoelastic index, from the cuff pressure and the pulse wave amplitude (S18). The previously obtained area and the lately obtained area are compared with each other to evaluate the vascular endothelial function (S19). The comparison is performed by obtaining a result of a division in which the previously obtained area is divided by the later obtained area.

As described above, occlusion of the artery is performed by the first cuff 11, and the pulse wave is measured in a different portion by the second cuff 51. As described in JP-A-2009-273870 by the inventors of the present patent application, the pulse wave may be measured in the same portion by the cuff for performing occlusion of the artery.

Figure 5:
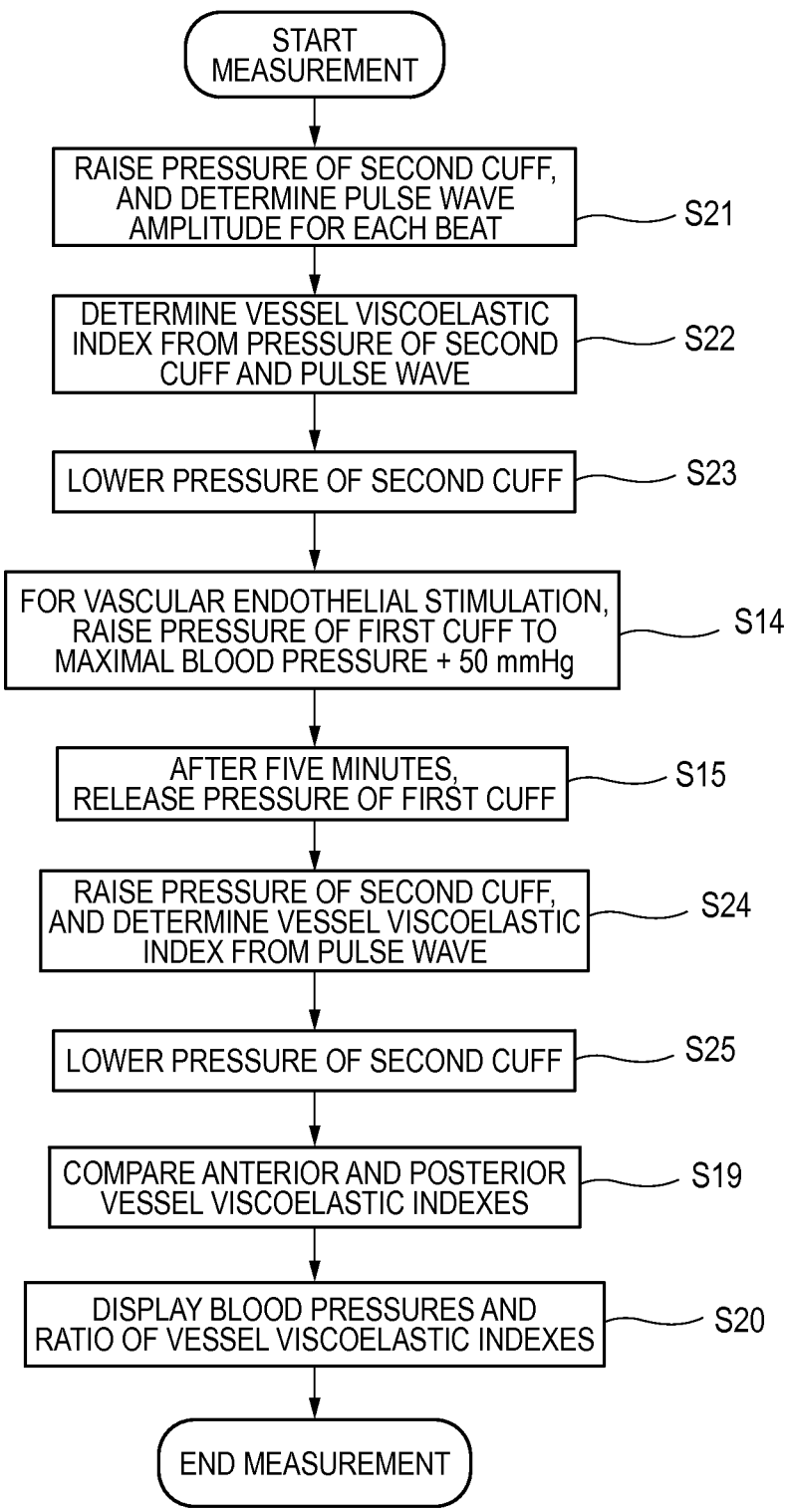
FIG. 5 is a flowchart illustrating a pulse wave measuring operation which is performed in a process of pressurizing the cuff pressure by the embodiment of the apparatus for evaluating a vascular endothelial function according to the presently disclosed subject matter.

In the embodiment, the pulse wave is measured during the process of depressurizing the cuff pressure. Alternatively, as shown in the flowchart of FIG. 5, the measurement may be performed during the process of pressurizing the cuff pressure. Namely, under the control of the controlling unit 20, in the state where the second valve 53 is closed, the air is sent from the second pump 52 to the second cuff 51 to raise the cuff pressure, and, during the process of pressurizing the cuff pressure, the pulse wave amplitude for each beat is detected by the pulse wave detecting unit 32 (S21).

Furthermore, the cuff pressure detecting unit 31 detects the cuff pressure from the output of the second pressure sensor 54, and, on the basis of the cuff pressure and the pulse wave, the analyzing unit 33 obtains the vessel viscoelastic index (S22). The area of the pulse wave functioning as the vessel viscoelastic index is obtained by statistically processing the area of the pulse wave which is obtained in the pressurization period.

After the pressurization period which is adequately set, the second valve 53 is opened to lower the pressure of the second cuff 51 (S23), processes such as the occlusion of the artery by the first cuff 11 and its cancellation in steps S14 and S15 which are identical with those of the embodiment shown in the flowchart of FIG. 4 are performed, the pressure of the second cuff 51 is then raised, and, during the process of raising the cuff pressure of the second cuff 51, the pulse wave amplitude for each beat is detected by the pulse wave detecting unit 32 (S24). The process in step S24 is identical with steps S21 and S22. After the process, the pressure of the second cuff 51 is lowered (S25), and processes of steps S19 and S20 which are identical with those of the embodiment shown in the flowchart of FIG. 4 are performed.

In FIGS. 4 and 5, as described above, the pulse wave amplitude for each beat is determined during the lowering of the pressure of the second cuff (S12, S17), or the rising of the pressure (S21, S24). Alternatively, the pulse wave amplitude for each beat may be determined in a state where the pressure of the second cuff is kept constant (at a constant pressure). For example, the constant pressure is about 20 mmHg. Alternatively, the pulse wave may be detected during the pressurization period T when the occlusion of the artery is performed, the vessel viscoelastic index may be obtained based on the detected pulse wave, the pulse wave may be detected during the measurement period Tp or Ta, the vessel viscoelastic index may be obtained based on the detected pulse wave, and the vessel viscoelastic indexes obtained during the two zones may be compared with each other.

In the case where, in the state where the pressure of the second cuff is kept constant (at a constant pressure), the pulse wave amplitude for each beat is determined, the first cuff and the second cuff may be identical with each other, or a single cuff may be used. In such a case, the configuration of FIG. 1 is modified so that the second cuff 51, the second pump 52, the second valve 53, and the second sensor 54 are removed away, the first cuff 11 is provided with the function of the second cuff 51, the first pump 12 is provided with the function of the second pump 52, the first valve 13 is provided with the function of the second valve 53, and the first sensor 14 is provided with the function of the second sensor 54.

The apparatus for evaluating a vascular endothelial displays the vessel viscoelastic indexes which are obtained as described above, together with a result of a comparison of the indexes, on the displaying unit 40. As the blood pressure value, the value of a preset one of the measurement periods Tp and Ta using the second cuff 51 is displayed. The apparatus for evaluating a vascular endothelial may produce a graph in which the value of the vessel viscoelastic index is plotted in time series, and display the graph on the displaying unit 40. Furthermore, the apparatus may produce a graph in which a ratio of the anterior vessel viscoelastic index to the posterior vessel viscoelastic index is plotted in time series, and display the graph on the displaying unit 40. Moreover, history information of data of obtained vessel viscoelastic indexes may be caused to remain, and the trend may be displayed on the displaying unit 40 in the form of a list. From the data of obtained vessel viscoelastic indexes, a graph may be produced, and the trend may be displayed on the displaying unit 40.

Figure 6A:
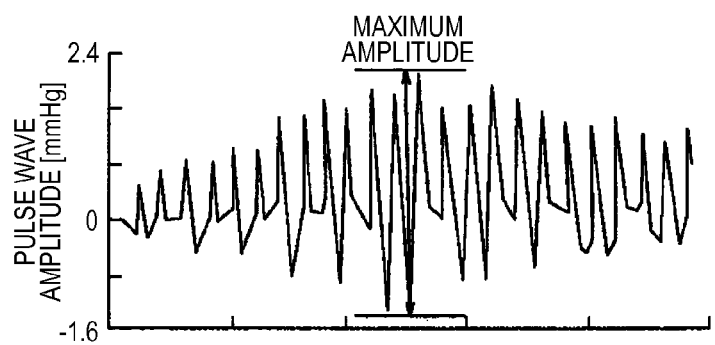
FIGS. 6A to 6D are views illustrating examples of the vessel viscoelastic index which can be used in the embodiment of the apparatus for evaluating a vascular endothelial function according to the presently disclosed subject matter.
Figure 6B:
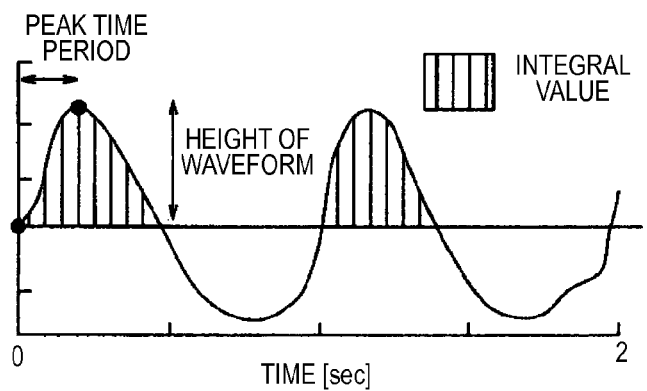
Figure 6C:
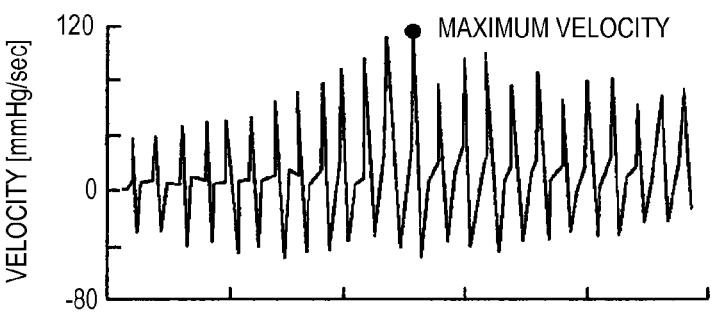

In the embodiment, the area of the pulse wave is obtained as the vessel viscoelastic index. Alternatively, the velocity of the pulse wave may be used as the vessel viscoelastic index. For example, the pulse wave in the vicinity of the maximum pulse wave amplitude shown in FIG. 6A is differentiated with time, and the velocity of the pulse wave shown in FIG. 6C is obtained. A statistical process is performed on the velocity. As the statistical process, a technique in which the maximum velocity is obtained may be employed.

Figure 6D:
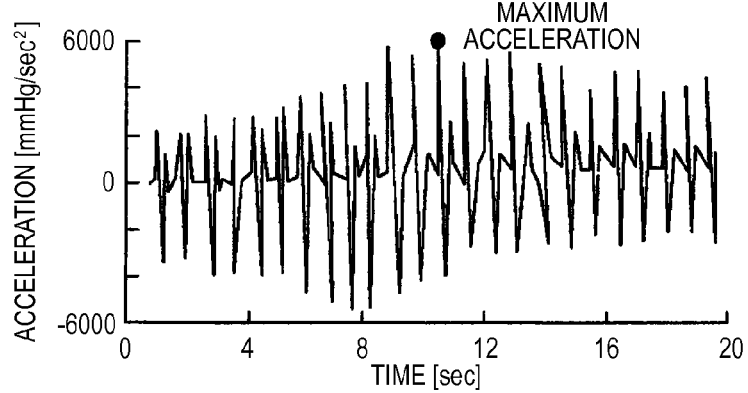

Alternatively, the acceleration of the pulse wave may be used as the vessel viscoelastic index. For example, the pulse wave in the vicinity of the maximum pulse wave amplitude shown in FIG. 6A is doubly differentiated with time, and the acceleration of the pulse wave shown in FIG. 6D is obtained. A statistical process is performed on the acceleration. As the statistical process, a technique in which the maximum acceleration is obtained may be employed.

Alternatively, the peak time period may be used as the vessel viscoelastic index. For example, it is assumed that FIG. 6B is an enlarged view of the pulse wave in the vicinity of the maximum pulse wave amplitude shown in FIG. 6A. As shown in FIG. 6B, the time period from the zero cross point of a waveform to the peak point of the waveform is set as the peak time period, and the peak time period may be used as the vessel viscoelastic index. A statistical process is performed on the peak time period. As the statistical process, a technique in which the maximum peak time period is obtained, or that in which the average of peak time periods of a predetermined number of waveforms may be employed. Alternatively, the height of the waveform shown in FIG. 6B may be used. The height of the waveform means the height from the zero cross point of the waveform to the peak point.

Figure 8A:
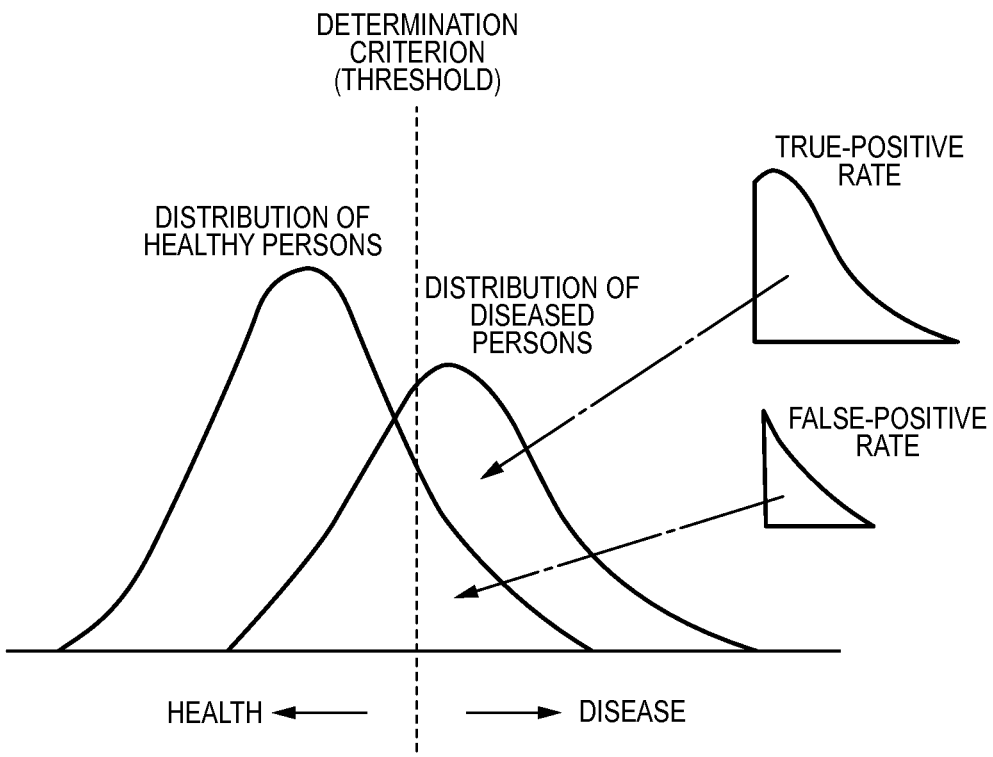
FIGS. 8A and 8B are views illustrating the ROC analysis which is a verification technique used in a verification of the determination accuracy of the embodiment of the apparatus for evaluating a vascular endothelial function according to the presently disclosed subject matter.
Figure 8B:
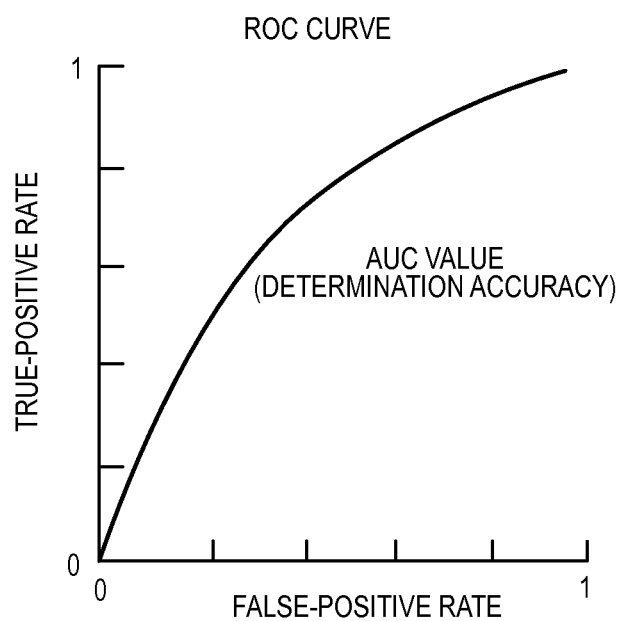
Figure 9:
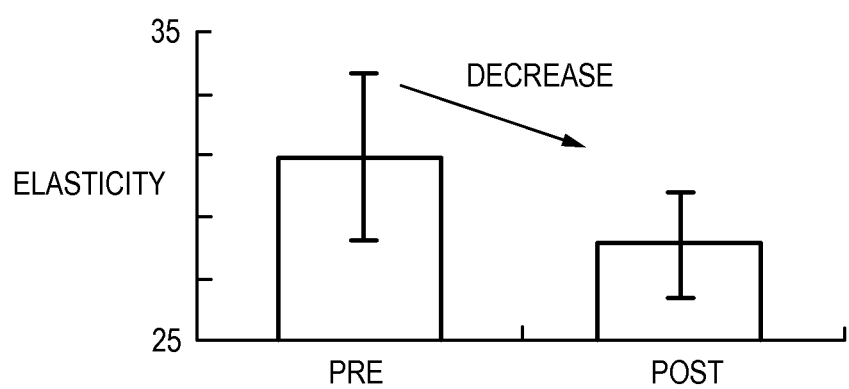
FIG. 9 is a view illustrating results of measurements of changes of the elasticity and the viscosity in the vasodilation before and after the pressure stimulation, by a related-art FMD.
Figure 9:
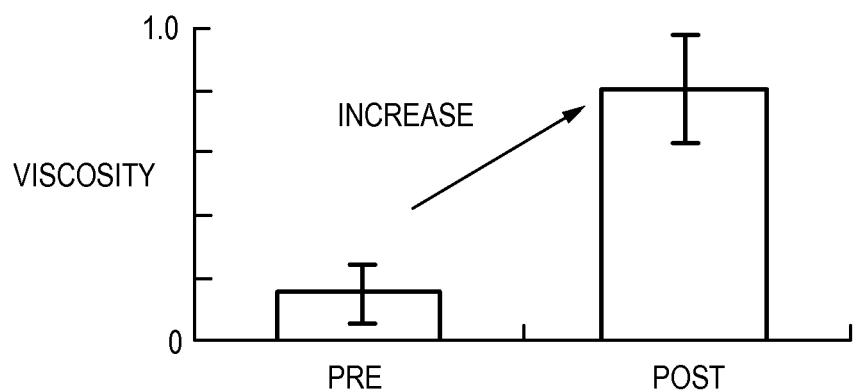
Figure 10:
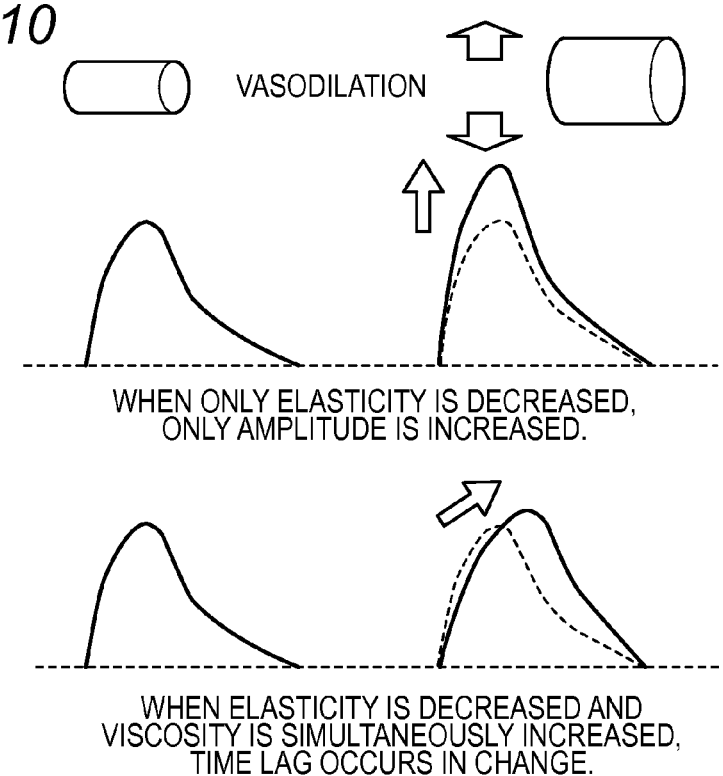
FIG. 10 is a view illustrating examples of the amplitude waveform of the pulse wave in the measurements of FIG. 9.

A verification of the determination accuracy was performed with respect to the technique in which the vascular endothelial function is evaluated by a comparison using vessel viscoelastic indexes which, as described above, are obtained from pulse waves that are detected in any two of zones, i.e., before the pressure stimulation, during the pressure stimulation, and after the pressure stimulation. A ROC analysis was used as the method of the verification. In the analysis, in the case where, as shown in FIG. 8A, a determination criterion (threshold) is set with respect to a distribution of healthy persons, and a distribution of diseased persons, the true-positive rate and false-positive rate which are shown in the figure are obtained. The true-positive rate means the rate of patients who are correctly determined to be diseased, and the false-positive rate means the rate of patients who are erroneously determined to be diseased. When the abscissa indicates the false-positive rate, the ordinate indicates the true-positive rate, true- and false-positive rates are obtained while varying the determination criterion, and the rates are plotted, the ROC curve is obtained as shown in FIG. 8B. In the ROC curve, it can be verified that the more quickly the curve rises, the more excellent the technique is.

Figure 7:
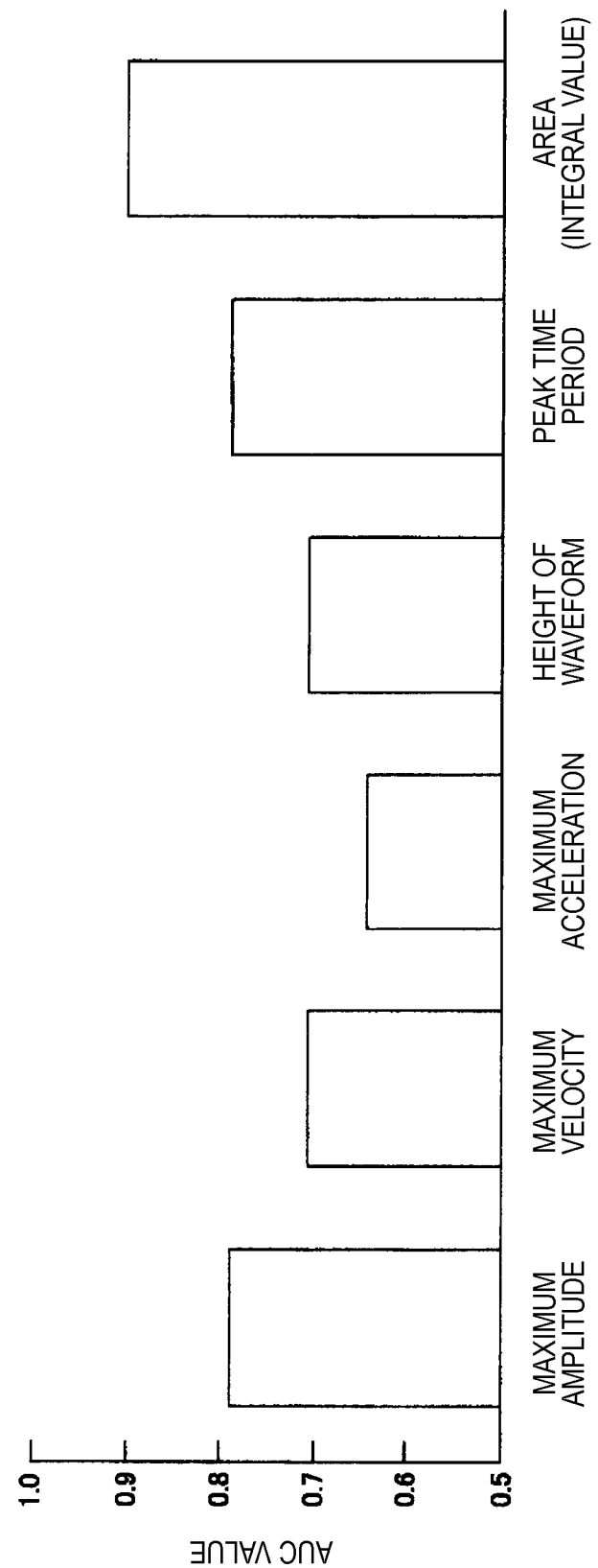
FIG. 7 is a view illustrating results of a ROC analysis related to the examples of the vessel viscoelastic index which can be used in the embodiment of the apparatus for evaluating a vascular endothelial function according to the presently disclosed subject matter.

With respect to the AUC value which is the ratio of the areas above and below the ROC curve, when specific examples of vessel viscoelastic indexes are arranged, FIG. 7 is obtained. According to FIG. 7, it is seen that the area (integral value) used in the embodiment of the presently disclosed subject matter provides a very excellent evaluation technique. In FIG. 7, the maximum amplitude which functions as a vessel viscoelastic index in the prior patent application is about 0.8 or sufficiently high, and also the maximum velocity, the maximum acceleration, the height of the waveform, and the peak time period are 0.6 or more. Therefore, it has been verified that the present technique is sufficiently useful.

In the above, the measurement periods Tp and Ta for the pulse wave measurement using the second cuff 51 are realized before and after the pressurization period T for vascular endothelial stimulation, and one measurement is performed in each of the measurement periods Tp and Ta for the pulse wave measurement. Alternatively, a plurality of measurements may be performed in each of the measurement periods. In the alternative, the numbers of the anterior and posterior measurements may be different from each other. In the measurement periods Tp and Ta, the cuff pressure may be raised from an atmosphere pressure to a pressure that is equal to or higher than a mean blood pressure of the subject, and then lowered to a pressure that is equal to or lower than a minimal blood pressure of the subject.

According to the presently disclosed subject matter, continuous pressure stimulation is performed on a body part of the subject for the predetermined time, and the analyzing unit evaluates the vascular endothelial function by comparing vessel viscoelastic indexes of pulse waves before and after the pressure stimulation with each other. Therefore, the configuration and the measurement technique are simplified, and, since the pulse waves before and after the pressure stimulation have information of the viscoelastic characteristics of the vessel, the comparison of the pulse waves enables the evaluation of the vascular endothelial function to be performed highly accurately.

Figure 11:
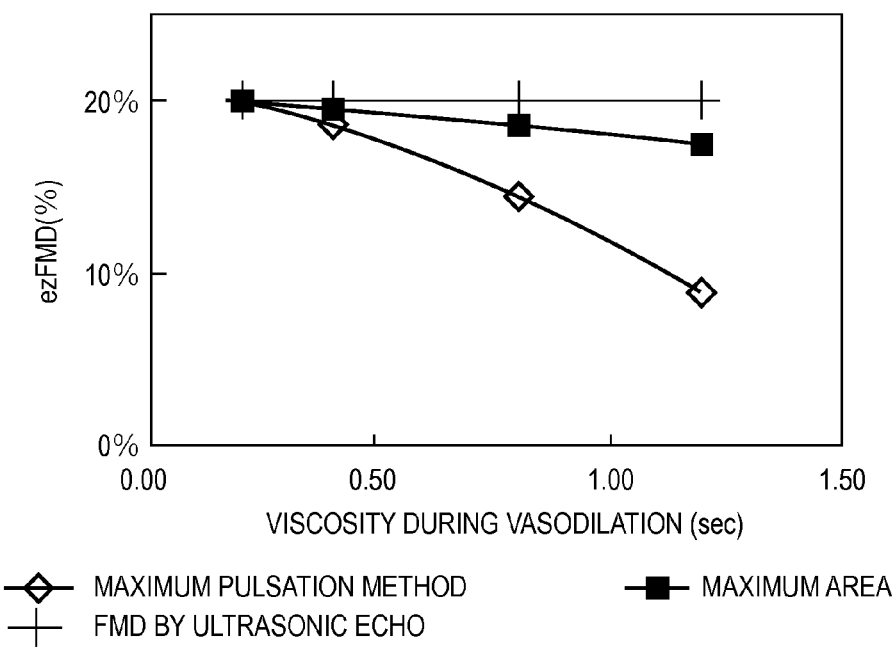
FIG. 11 is a view illustrating influences which were obtained in a simulation, and which were caused by the passage of time and a change in the viscosity after the pressure stimulation.

FIG. 11 shows influences which, in a simulation waveform, are applied to the amplitude and area of the pulse wave by changes in the viscosity and elasticity values, together with the passage of time. As shown in FIG. 11, the FMD is not affected by a change in the viscosity due to the passage of time. By contrast, in the technique (Maximum Area Method) of the presently disclosed subject matter in which the maximum area of the pulse wave that is the viscoelastic index excluding the amplitude of the pulse wave, although affected by the viscosity due to the passage of time, the measurement results were similar to those of the FMD, and the deviation from the FMD was more improved than that in the technique (Maximum Pulsation Method) in which the maximum amplitude of the pulse wave is measured.

What is claimed is:

1. An apparatus for evaluating a vascular endothelial function, the apparatus comprising:
   a cuff pressure controlling unit configured to perform continuous pressure stimulation on a part of a body of a subject for a predetermined time, by using a cuff adapted to be wrapped around the part of the body of the subject;
   a cuff pressure detecting unit configured to detect a cuff pressure from an output of a pressure sensor connected to the cuff;
   a pulse wave detecting unit configured to detect a pulse wave from the output of the pressure sensor; and
   an analyzing unit configured to evaluate the vascular endothelial function by comparing vessel viscoelastic indexes which are obtained from the pulse wave detected in two zones selected from among a plurality of zones comprising before the pressure stimulation, during the pressure stimulation, and after the pressure stimulation,
   wherein the vessel viscoelastic indexes comprise one of velocities, areas, accelerations, and peak time periods of the pulse wave,
   wherein the vessel viscoelastic indexes exclude a maximum amplitude of the pulse wave, and
   wherein the analyzing unit performs statistical processing on the vessel viscoelastic indexes in which a maximum value of the vessel viscoelastic index is obtained and compares the vessel viscoelastic indexes on which the statistical processing has been performed.

2. The apparatus according to claim 1, wherein the pressure stimulation is pressurization at a substantially constant pressure for the predetermined time.

3. The apparatus according to claim 1, wherein the cuff pressure controlling unit performs at least one time processing in which, at least one of before and after the pressure stimulation, the cuff pressure is raised from an atmosphere pressure to a pressure that is equal to or higher than a mean blood pressure of the subject, and then lowered to a pressure that is equal to or lower than a minimal blood pressure of the subject.

4. The apparatus according to claim 1, wherein the analyzing unit evaluates the vascular endothelial function by comparing a vessel viscoelastic index excluding the maximum amplitude of the pulse wave which is obtained in a constant-pressure process in which a predetermined pressure of the cuff pressure, which is attained in a pressurization process, is maintained for a predetermined time period, with a vessel viscoelastic index excluding the maximum amplitude of the pulse wave which is obtained before or after the pressure stimulation.

5. The apparatus according to claim 1, wherein the statistical processing is processing in which a maximum value of a vessel viscoelastic index excluding the maximum amplitude of the pulse wave in a process of pressurizing or depressurizing the cuff pressure is obtained.

6. The apparatus according to claim 1, wherein the statistical processing is processing in which a maximum value of a vessel viscoelastic index excluding the maximum amplitude of the pulse wave in a constant-pressure process of the cuff pressure is obtained.

7. The apparatus according to claim 1, wherein the statistical processing is processing in which an average value of a maximum value of a vessel viscoelastic index excluding the maximum amplitude of the pulse wave obtained during the change of the cuff pressure is obtained.

8. The apparatus according to claim 1, wherein the statistical processing is processing in which an average value of a maximum value of a vessel viscoelastic index excluding the maximum amplitude of the pulse wave obtained when the cuff pressure is constant is obtained.

9. The apparatus according to claim 1, further comprising a displaying unit, wherein
the analyzing unit calculates a blood pressure value from the pulse wave, and
the displaying unit displays the blood pressure value together with a result of a comparison by the analyzing unit.

10. The apparatus according to claim 1, wherein
the cuff includes a first cuff which is adapted to be wrapped around a first part of the body of the subject, and a second cuff which is adapted to be wrapped around a second part of the body of the subject,
the cuff pressure controlling unit controls pressurization and depressurization of one of the first and second cuffs, and
the cuff pressure detecting unit detects the cuff pressure from an output of a pressure sensor connected to the other of the first and second cuffs.

11. The apparatus according to claim 10, wherein the first and second cuffs are placed on one of four limbs of the body of the subject.

12. The apparatus according to claim 1, further comprising: an output unit which outputs the processed vessel viscoelastic indexes.

13. The apparatus according to claim 1, wherein the analyzing unit outputs blood pressures and ratio of the vessel viscoelastic indexes to a display.

14. The apparatus according to claim 1, further comprising: an output unit which outputs at least one from among: a graph generated by the analyzing unit from the processed vessel viscoelastic indexes and a trend generated from the processed viscoelastic indexes, each of which comprise values of the vessel viscoelastic indexes plotted in time series.

15. The apparatus according to claim 1, wherein the vessel viscoelastic indexes are the areas of the pulse wave, wherein an area of the pulse wave from among the areas of the pulse wave is an area surrounded by, when the pulse wave is divided into upper and lower portions by a zero cross line of the pulse wave, which is a line from a zero cross point to next zero cross point of the pulse waveform.

16. The apparatus according to claim 1, wherein the vessel viscoelastic indexes are the peak time periods of the pulse wave and wherein a time period from a zero cross point of the pulse waveform to a next peak point of the pulse waveform is set as a peak time period.

* * * * *